United States Patent [19]

Thoma et al.

[11] Patent Number: 4,693,252
[45] Date of Patent: Sep. 15, 1987

[54] DEVICE FOR GENERATING DRY, COLD GAS FLOW

[75] Inventors: Klemens Thoma, Krefeld-Huls; Wolfgang Volker, Tonisvorst, both of Fed. Rep. of Germany

[73] Assignee: Messer Griesheim GmbH, Fed. Rep. of Germany

[21] Appl. No.: 821,347

[22] Filed: Jan. 22, 1986

[30] Foreign Application Priority Data

Feb. 27, 1984 [DE] Fed. Rep. of Germany ....... 3506932

[51] Int. Cl.[4] ............................................. A61F 7/00
[52] U.S. Cl. ...................................... 128/400; 34/20; 62/50
[58] Field of Search ................ 128/303.1, 400; 34/20; 62/50

[56] References Cited

U.S. PATENT DOCUMENTS 1,644,966 10/1927 Weski .................................. 128/400
3,507,283 4/1970 Thomas ........................... 128/303.1

FOREIGN PATENT DOCUMENTS 2026324 2/1980 United Kingdom ............. 128/303.1

Primary Examiner—Anton O. Oechsle
Attorney, Agent, or Firm—Harold Pezzner

[57] ABSTRACT

A device for generating a dry cold gas flow by evaporating a low-boiling liquefied gas for cold therapy for rheumatic diseases includes a vessel for accommodating the low-boiling liquefied gas. A hose line is connected to the vessel with an interchangeable treatment nozzle for distribution of the evaporated gas. The vessel has only a small storage volume, and in the vicinity of its bottom, it is provided with an adjustable electrical heater for evaporation of the liquefied gas. The hose line is connected to the vessel by means of an adjustable electrical heating line.

7 Claims, 1 Drawing Figure

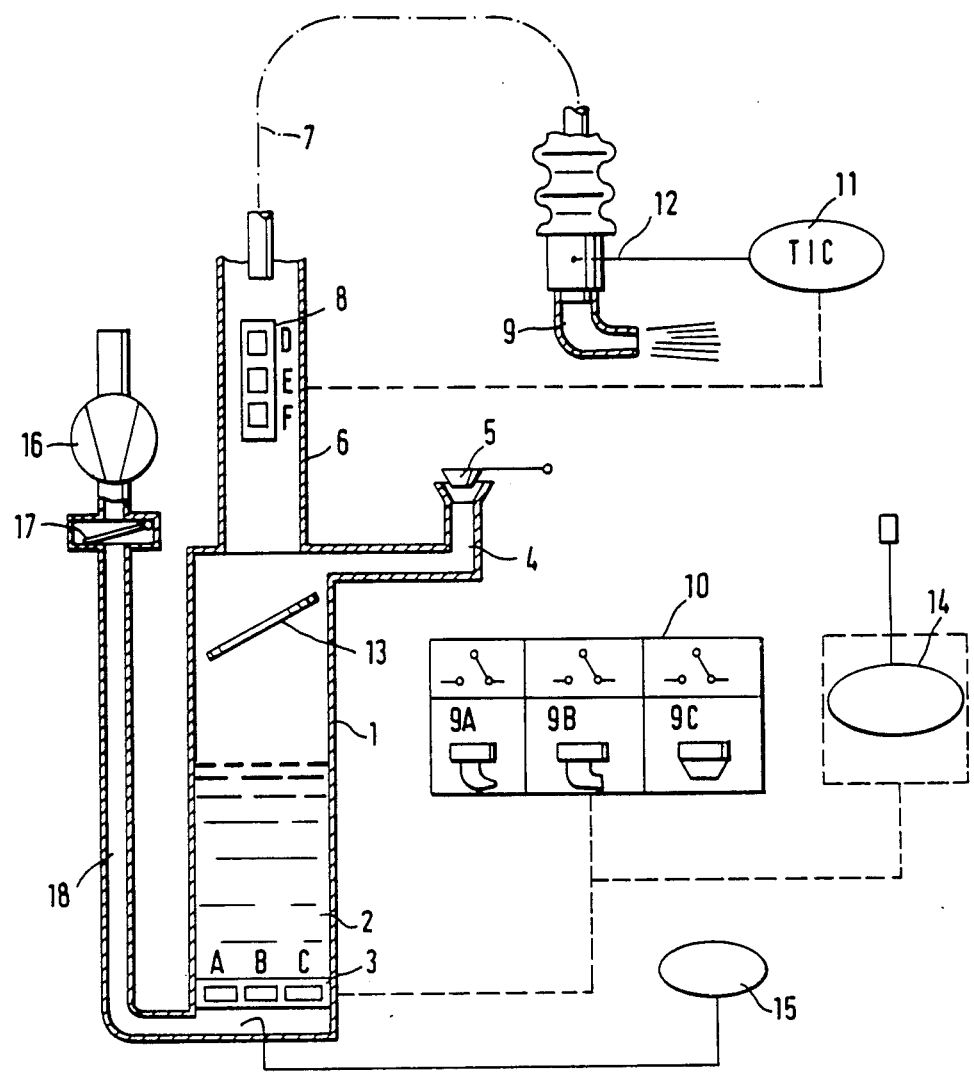

ered e.g. for 0.9 kw, 1.35 kw, and 1.8 kw. Correspondingly, the heating register 8 has output levels of 100 W,

DEVICE FOR GENERATING DRY, COLD GAS FLOW

BACKGROUND OF THE INVENTION

The invention concerns a device for generating a dry, cold gas flow by evaporating a low-boiling liquefied gas for purposes of cold therapy for rheumatic diseases.

In past years, liquid nitrogen has become increasingly accepted as a refrigerant for cold therapy for rheumatic diseases. In many cases, evaporated liquid nitrogen is hereby mixed with air or oxygen in order to obtain a treatment gas at the desired temperature. Such devices are shown in the German disclosure documents Nos. 32 42 881 and 28 39 214. With respect to these devices, it must generally be ascertained that no moisture freezes out of the ambient atmosphere and touches the body parts to be treated. In addition, there must be no dangerous oxygen depletion due to evaporation of too much liquid nitrogen. Relatively costly equipment is required in order to eliminate the moisture and to maintain a sufficient oxygen content. This renders the treatment equipment so expensive and voluminous that the use thereof is justifiable only in specific therapy centers. However, in these centers, it fulfills its purpose in a satisfactory manner.

However, there is a need not to limit the cold therapy for rheumatic diseases to specific therapy centers but to render this therapy possible in average medical office facilities and hospitals as well.

SUMMARY OF THE INVENTION

The object of the invention is to create a device with liquid nitrogen as a refrigerant medium for cold therapy for rheumatic diseases, which device is so easily and simply constructed that it can also be designed as mobile equipment.

The device according to the invention has two signficant characteristics. One characteristic consists therein that liquid nitrogen is used exclusively as treatment gas. This liquid nitrogen is completely dry, so that no problems can be caused due to moisture freezing out.

However, in order to achieve the desired treatment temperature, two-fold regulated heating is required, namely once for evaporation of the nitrogen, and thereafter for heating the evaporated nitrogen to the desired treatment temperature. The second significant characteristic consists therein that the storage volume of the vessel accommodating the low boiling liquefied gas, i.e. normally liquid nitrogen, is made so small that no unacceptable oxygen depletion can occur, even with complete evaporation of the liquefied gas. For this purpose, a storage volume of max. 6 liters is suitable when nitrogen is used. Even with complete evaporation of 6 liters of liquid nitrogen in a patient room, there occurs no dangerous depletion of the oxygen content. On the other hand, 6 liters are sufficient for treatment of 3 to 6 patients.

THE DRAWINGS

The single FIGURE schematically illustrates one example of the device according to the invention.

DETAILED DESCRPTION

The device consists of a vessel 1 for accommodating the liquid nitrogen 2. On the bottom of the vessel 1, there is an electrical heater 3, the output of which can be regulated by turning the heater windings A, B. and C on or off. The vessel 1 is filled with liquid nitrogen by means of a submerged pump, through the connector 4. The connector 4 is closed by means of a conical valve 5. A permanent magnet holds the seal of the conical valve 5 against the overpressure of approximately 50 mbar in the system.

Connected to the gas space of the vessel 1, there is a heating line 6, from which a hose line 7 is led on. In the heating line 6, there is an electrical heating register 8, the output of which can be regulated by turning the heater windings D, E, and F on or off. The hose line 7 ends in the interchangeable treatment nozzle 9. The interchangeable treatment nozzles 9 have different cross sections. In order to achieve that the speed of the exiting gas flow is approximately the same with all nozzles, different heat outputs of the electrical heater 3 are required. In each case, the required heat output is set automatically by means of an electrical connection when the treatment nozzle 9 is inserted. This is symbolically represented by the block 10 with the three different treatment nozzles 9A, 9B, and 9C. The heater windings of the heating register 8 are also turned on in a similar manner. Although the heat output of the heating register 8 is much lower than that of the electrical heater 3, it is necessary to adjust the heat output to the cross section of the nozzle in this case as well, since the temperature regulation device would otherwise be overtaxed. The temperature regulation is achieved by means of the temperature sensor 12 in the area of the treatment nozzle 9, and the actual temperature regulator 11, which affects the heating register 8. The heater windings D, E, and F of the heating register 8 are wires which are located directly in the nitrogen flow. Hereby, the inert mass is extremely low, the response time correspondingly short. Consequently, the temperature regulation is extremely rapid and exact. In the gas space of the vessel 1, there is also a baffle plate 13, which prevents drops of liquid from being carried along into the heating line 6.

Although oxygen monitoring of the treatment room is not required per se, it can be achieved in a simple manner, if it is not to be excluded. A corresponding oxygen monitoring device 14 then affects the control system in such a manner that the heater 3 and the heating register 8 are turned off at a border value of less than 17% oxygen by volume.

After completion of the treatment, ambient air is blown through the entire device. However, any still existing liquid nitrogen must first be removed, since oxygen could concentrate thereon in a dangerous manner. This is accomplished by means of the level monitor 15, which does not release the blower air until a level limit for the liquid nitrogen 2 has been reached. The blower air is sucked in through the blower 16 and led through the vessel 1, the heating line 6, the hose line 7, and the treatment nozzle 9 by means of a flap 17 and the connector 18. The flap 17 prevents cold gas from escaping during the therapy. Ambient air is blown through the device until it has assumed ambient temperature. The reheating of the device can also be achieved by circulating evaporated liquid nitrogen.

Preferably, the device according to the invention is conceived as mobile equipment. It is advantageously designed so that a power supply of 220 V and 2 kw is sufficient. Thereby, the electrical heater 3 can be graduated e.g. for 0.9 kw, 1.35 kw, and 1.8 kw. Correspondingly, the heating register 8 has output levels of 100 W, 150 W, and 200 W. Although it is advantageous to automate the application of heat output of the individual treatment nozzles, the device can also easily be designed with manual adjustment of the heat output. For specific applications, continuous change of the heat output can also be provided. Overfilling the vessel 1 can be prevented by means of a limiter for operational time, which is connected to the submerged pump. Naturally, it is also possible to use other filling systems instead of a submerged pump, e.g. containers with built-in pressure build-up, in which the filling occurs via a magnet valve.

Admittedly, the specific operational costs of the device according to the invention are relatively high since, due to the fact that the entire quantity of nitrogen is electrically heated to the desired treatment temperature, the cold of the liquid nitrogen is only incompletely utilized. However, since the device is conceived only for occasional individual treatments and not for continuous operation, the slightly higher operational costs are inconsiderable when compared to the advantages. These advantages include simple technical structure, mobility, small size, and readiness for use at any time.

The use of liquid nitrogen is common in cold therapy for rheumatic diseases. The liquid nitrogen is either used to cool air to the desired treatment temperature, whereby the mositure frozen out must be removed permanently or periodically, or the evaporated nitrogen is mixed with gaseous oxygen in such a manner that the mixture corresponds to that of air. In this case, oxygen depletion in the treatment room must be avoided. Although this type of equipment does fulfill its purpose, it is costly due to the additional devices required for removal of mositure or for generating the mixture, and thus, it is suitable only for therapy centers, e.g. in hospitals.

In order to make it possible to also provide cold therapy in normal medical offices by means of a small, simple device, the treatment gas is obtained exclusively from liquid nitrogen (2). Hereby, the liquid nitrogen is stored in a vessel (1) with electrical heating (3). The heat output is adjusted either manually or automatically by means of the inserted treatment nozzle (9). In a heating line (6), the evaporated nitrogen is heated to the desired treatment temperature, with application of a temperature sensor (12) with related control, which is located in the treatment nozzle. Unacceptable oxygen depletion is prevented thereby that the capacity of the vessel is limited to maximum 6 liters.

What is claimed is:

1. In a device for generating a dry cold gas flow by evaporating a low-boiling liquefied gas for cold thereapy for rheumatic diseases, with a vessel for accomodating the low-boiling liquefied gas, a hose line one end of which is connected to the vessel, and a plurality of interchangeable treatment nozzles of different cross sections for distribution of the evaporated gas attachable to the other end of the hose, the improvement being in that said vessel has only a small storage volume, the bottom of said vessel being provided with an adjustable electrical heater for evaporation of the liquefied gas, means for adjusting the output of said electrical heater to ensure essentially the same gas exiting speed regardless of which nozzle is attached, and said one end of said hose line being connected to said vessel by means of an adjustable electrical heating line for heating the evaporated gas to the desired temperature.

2. Device according to claim 1, characterized thereby that said means for adjusting the output of said electrical heater in said vessel is via an electrical connection when said interchangeable treatment nozzles are inserted.

3. Device according to claim 2, characterized thereby that the output of said electrical heating line is controlled by means of a temperature sensor adjacent the other end of said hose.

4. Device according to claim 3, characterized thereby that the maximum storage volume of said vessel does not exceed about six liters.

5. Device according to claim 2, characterized thereby that the maximum storage volume of said vessel does not exceed about six liters.

6. Device according to claim 1, characterized thereby that the output of said electrical heating line is controlled by means of a temperature sensor adjacent the other end of said hose.

7. Device according to claim 1, characterized thereby that the maximum storage volume of said vessel does not exceed about six liters.

* * * * *